(12) United States Patent
Thompson et al.

(10) Patent No.: US 7,842,491 B2
(45) Date of Patent: Nov. 30, 2010

(54) DETERMINATION OF METAL IONS IN SOLUTION BY PHOTOLUMINESCENCE ANISOTROPY

(75) Inventors: Richard B. Thompson, 7106 Bristol Rd., Baltimore, MD (US) 21212; Daniel Elbaum, Newton, MA (US); Vincent L. Feliccia, Arnold, MD (US); David Christianson, Media, PA (US); Marcia W. Patchan, Columbia, MD (US); Zhengfang Ge, Rockville, MD (US); Badri P. Maliwal, San Francisco, CA (US)

(73) Assignee: Richard B. Thompson, Baltimore, MD (US)

( * ) Notice: Subject to any disclaimer, the term of this patent is extended or adjusted under 35 U.S.C. 154(b) by 1437 days.

(21) Appl. No.: 10/982,956

(22) Filed: Nov. 8, 2004

(65) Prior Publication Data

US 2005/0250170 A1 Nov. 10, 2005

(51) Int. Cl.
*C12Q 1/34* (2006.01)
*C12Q 1/00* (2006.01)
*G01N 21/00* (2006.01)
*G01N 33/20* (2006.01)

(52) U.S. Cl. .................. 435/232; 436/81; 435/975; 435/18

(58) Field of Classification Search ............ 435/18, 435/232, 975; 436/81
See application file for complete search history.

(56) References Cited

U.S. PATENT DOCUMENTS

| | | | |
|---|---|---|---|
| 4,261,968 A | 4/1981 | Ullman et al. | |
| 4,762,799 A | 8/1988 | Seitz et al. | |
| 5,154,890 A | 10/1992 | Mauze et al. | |
| 5,459,040 A | 10/1995 | Hammock et al. | |
| 5,464,587 A | 11/1995 | Lippitsch et al. | |
| 5,516,864 A | 5/1996 | Kuhn et al. | |
| 5,545,517 A | 8/1996 | Thompson et al. | |
| 5,606,045 A | 2/1997 | Dandliker et al. | |
| 5,952,236 A | 9/1999 | Thompson et al. | |

OTHER PUBLICATIONS

C.H. Sueltor, *Biochemistry*, 1967, 6, 418-423.
C.W. Hoagstrom et al., *J. Biol. Chem.*, 1969, 244, 5967-5971.
P.L. Coleman et al., *Biochemistry*, 1972, 11, 1010-1018.
J. Schlessinger et al., *Biochemistry*, 1975, 14, 255-262.
J.E. Scheffler et al., *Biochemistry*, 1986, 25, 6659-6665.
E.L. Pugh et al., *Biochim. Biophys. Acta*, 1989, 985, 255-265.
Z. Ma et al., *Zhongguo Shouyi Xuebao*, 1996, 16, 585-590.
G. Mei et al., *Protein Sci.*, 1996, 5, 2248-2254.
D. Bhatnagar et al., *Biochemistry*, 1983, 22, 6310-6317.
D. Genest et al., *Biochimie*, 1984, 66, 631-638.
J.R. Lakowicz et al, *J. Biol. Chem.*, 1984, 259, 10967-10972.
M.R. Eftink et al., *Biochemistry*, 1986, 25, 6631-6637.
D.A. Deranleau, *J. Am. Chem. Soc.*, 1975, 97, 1218-1224.
K. Ugurbil et al., *Biochemistry*, 1977, 16, 895-901.
P. VanDerlijn et al., *Proc. Natl. Acad. Sci. U.S.A.*, 1978, 75, 4204-4208.
R.W. Henkens et al., *Biochemistry*, 1982, 21, 5918-5923.
J. Andrews e tal., *Archives of Biochemistry and Biophysics*, 1982, 214, 386-396.
W.B. Dandliker et al., *Immunochemistry*, (1973) 10, 219-227.
T.M. Eads et al., *J. Mol. Biol.*, (1984) 179, 55-81.
D. Elbaum et al., *J. Am. Chem. Soc.*, (1996) 118, 8381-8387.
J. Moratal et al., *J. Chem. Soc. Daton Trans.*, (1991) 3393-3399.
R.B. Thompson et al., *Journal of Biomedical Optics*, (1996) 1, 131-137.
R.B. Thompson et al., *SPIE*, (1996) 2680, 47-56.
R.B. Thompson et al., *Analytical Chmistry*, (1993), 65, 730-734.
R.B. Thompson et al., *SPIE*, (1993), 2068, 296-306.
R.B. Thompson et al., *Analytical Biochemistry*, (1995), 227, 123-128.
R.B. Thompson et al., *Journal of Fluorescence*, (1995), 5, 123-130.
G. Weber, *J. Biochem*, (1952), 51, 145-155.
G. Weber, *J. Biochem*, (1952), 51, 155-167.
D. Bhatnager et al., *Biochemistry*, (1983), Sec. 22, 6310-6317.
B.L. Ling et al., *J. Chromatogr*, (1990), 514, 189-198.
H.D. Husic et al., *Phytochem.*, (1993), 32, 805-810.
F. Wolf et al., *Chem. Abstr*, (1967), 67, 74440Y.
F.V. Bright Applied Spectroscopy, (1988), 42, 1245-1250.
K. Imai et al., *Anal. Chim. Acta*, (1989), 223, 299-308.
T.L. Kirley, *J. Biol. Chem.*, (1990), 265, 4277-4232.
T. Toyo'o ka et al., Anal. Chem. (1984), 56, 2461-2464.
R.F. Chen et al., J. Of Biological Chemistry, (1967), 242, No. 24, 5813-5823.

*Primary Examiner*—Jon P Weber
*Assistant Examiner*—Kailash C Srivastava
(74) *Attorney, Agent, or Firm*—Birch, Stewart, Kolasch & Birch, LLP (57) ABSTRACT

The invention relates to compositions and kits for homogeneous fluorescence polarization (anisotropy) assays for detecting and quantifying metal ions in solution. Metal-dependent binding of a fluorescent ligand to an unlabeled macromolecule effects a measurable change in anisotropy as will the binding of metal ions to a fluorescent labeled macromolecule. Binding of the fluorescent ligand to the unlabeled macromolecule is metal dependent with the change in anisotropy being proportional to the concentration of bound metal ions. Conversely, if the fluorescent label is first conjugated to a macromolecule and the macromolecule is subsequently stripped of metal ion, it may then be used to signal binding of metal ions. The covalently bound fluorescent label exhibits changes in anisotropy proportional to the concentration of bound metal ions. Kits comprise a fluorescent molecule and a macromolecule.

8 Claims, 9 Drawing Sheets

DETERMINATION OF METAL IONS IN SOLUTION BY PHOTOLUMINESCENCE ANISOTROPY

STATEMENT AS TO RIGHTS TO INVENTIONS MADE UNDER FEDERALLY SPONSORED RESEARCH AND DEVELOPMENT

This invention was made with the support of the U.S. Government under Grant Nos. N00014-91-1572 and BES-9613556 awarded by the Office of Naval Research and the National Science Foundation, respectively. The Government has certain rights in this invention.

CROSS-REFERENCE TO A RELATED APPLICATION

This application claims priority under 35 U.S.C. §120 of U.S. Non-Provisional Application No. 09/942,708 filed on Aug. 31, 2001, now abandoned, and of U.S. Non-Provisional Application No. 09/071,351 filed on Apr. 30, 1998, now U.S. Pat. No. 6,284,544, the entire contents of which are hereby incorporated by This application further claims priority to U.S. Provisional Application No. 60/045,289 filed on May 1, 1997 under 35U.S.C. §119(e)(1), the contents of which are herein incorporated by reference.

BACKGROUND OF THE INVENTION

1. Field of the Invention

The present invention relates to homogeneous methods for the detection, determination, and quantitative analysis of Cu (II), Zn (II) and other transition metal ions in solution and is based on the measurement of changes in fluorescence polarization (anisotropy) in response to metal ion concentration.

2. Background Art

Although many analytical methods exist for the quantitative analysis of metals, none utilize fluorescence polarization (anisotropy). Present analytical methods include graphite furnace atomic absorption spectroscopy, inductively coupled plasma atomic emission spectroscopy, mass spectroscopy, and numerous electrochemical and luminescence techniques. including phosphorescence, chemiluminescence and fluorescence. Common to all these methods are requirements for complex, expensive, sizable and fragile instrumentation; skilled operators; and elaborate experimental and separation procedures to achieve acceptable precision and accuracy.

At present, one skilled in the art would not find it obvious to utilize fluorescence polarization (anisotropy) for the quantitative analysis of metal ions in solution. It is well known in the art that most metal ions are not photoluminescent in solution. Even if we consider transition metal ions which have weak absorption bands in the uv/visible/near IR; the excitation of these metal ions with plane polarized light generally effects only depolarized fluorescence due to the radial symmetry of the absorbing species. Alternatively, if an indirect approach is used wherein the binding of a metal ion to a metallo-fluorescent indicator is monitored, one also finds little or no change in fluorescence polarization (anisotropy), as there is no change in the rotational motion of the fluorescent indicator in response to the binding of a metal ion. Even if the binding of the metal ion perturbs the fluorescence lifetime of the metal-free fluorescent indicator, the rotational motion of the indicator will probably be sufficiently rapid in comparison to its rate of emission that its emission will be completely depolarized whether the metal ion is present or not, resulting in an imperceptible change in fluorescence polarization. These representative and other difficulties have prevented the application of fluorescence polarization (anisotropy) to metal ion analysis in aqueous solutions.

The present invention extends for the first time the use of fluorescence polarization (anisotropy) for the detection and quantitative analysis of metal ions in aqueous solutions. This invention comes more than twenty-five years after the first application of fluorescence polarization (anisotropy) to the detection and quantitation of fluorescent labeled haptens and antigens with suitable antibodies. The present invention is not constrained by immunoassay reaction kinetics between labeled and unlabeled antigen or hapten but is simply predicated on the use of a photoluminescent indicator that will emit polarized light in a measurably different manner on the formation of a macromolecule-metal ion complex. A complex which in the preferred embodiments relies on either the metal dependent binding of a photoluminescent indicator to a macromolecule, or the binding of a metal ion to a macromolecule that has previously been labeled with a photoluminescent label. Additionally, the present invention is not constrained by the difficulties in raising antibodies to metal ions in solution.

3. Fluorescence Based Methods of Analysis

Assays for chemical entities based on changes in fluorescence intensity are well known. Ullman et al. (1981) (U.S. Pat. No. 4,261,968) discloses a proximity-dependent quenching homogeneous immunoassay wherein a fluorescent-labeled antibody is brought in contact with a sample containing a ligand (antigen or hapten) and a quencher-labeled ligand: the free ligand (of unknown concentration) and the quencher-labeled ligand (of known concentration) compete for the same antibody binding site. Quenching of the label's fluorescence emission is inversely proportional to the unlabeled antigen concentration, and serves as the measurement variable for determining the concentration of free ligand. Key to this method is the use of a ligand comprising two chromophores, termed a fluorescer-quencher pair with non-polymeric ligands being in the molecular weight range of 125 to 2,000, well above the atomic weights of most metal ions of interest. In relation to the present invention, Ullman does not teach the analysis of free metal ions in solution, or the use of polarization (anisotropy) as the measurement variable.

Numerous fluorometric methods for the analysis of metal ions in solution are known and vary primarily in terms of signal transduction. Metal ion concentrations may be transduced as changes in fluorescence intensity or as changes in the ratios of fluorescence intensities at two different wavelengths, or as changes in fluorescence lifetimes. Although, lifetime and ratiometric methods are qualitatively similar with respect to their freedom from spurious variations in fluorescence intensity, the physical measurement of fluorescence lifetime is costlier and technically more difficult than a simple intensity measurement, especially in the context of imaging applications. Regardless of these drawbacks, lifetime analysis has been preferred for reasons that include its broad dynamic test range in sample concentrations which may exceed five orders of magnitude in some cases (Szmacinski, H. and J. R. Lakowicz (1993) Anal. Chem. 65, 1668-1674); Thompson, R. B. and M. W. Patchan (1993) in *Proc. of the SPIE Conference on Chemical, Biochemical and Environmental Fiber Optic Sensors V*. R. A. Lieberman (Ed.) Bellingham, Wash., pp 296-306). Lifetime-based analysis also minimizes errors associated with optics, fluorophore concentration and detector sensitivity.

Methods based on the measurement of changes in fluorescence intensity include:

U.S. Pat. No. 4,762,799 (1988) to Seitz et al. which discloses an ionophore-based cation detection system wherein the concentration of selected alkali metal ions in an aqueous sample may be determined by detecting the fluorescence emission of a fluorescent anionic material.

U.S. Pat. No. 5,154,890 (1992) to Mauze and Rupp which discloses a homogeneous method for detecting the concentration of potassium ions in solution where the ion concentration is made proportional to an increase in fluorescence intensity on the formation of a complex comprising a fluorophore labeled molecule which selectively binds potassium ions.

U.S. Pat. No. 5,516,864 (1996) to Kuhn and Haugland which in part discloses the use of xanthylium-based dyes with metal-binding N,N'-diaryldiaza crown ethers, the best known class of ionophores, for the detection of alkali-metal ions in aqueous solution by measuring spectral changes in the fluorescence emission of an indicating dye.

These intensity based methods, however, are all sensitive to artifacts, as any change in fluorescence intensity, regardless of its origin may be misinterpreted as a change in concentration. Changes in light scattering, or variations in excitation light intensity and or photobleaching may easily be misinterpreted as a change in the concentration of the metal ion. Although the accuracy and precision of these methods may be improved through the use of internal fluorescent standards, or with the monitoring of excitation intensity or with the use of kinetic methods of analysis, careful and even repeated calibration of reagents and instrumentation are required to minimize spurious variations in signal intensity.

Recognizing, these limitations, Tsien and other researchers developed indicators whose fluorescent properties such as excitation or emission maxima, shifted in conjunction with the binding of analyte, permitting concentration to be described not in terms of absolute fluorescence intensity but rather in terms of a ratio of fluorescence intensities at different wavelengths (Tsien, R. Y. (1989) Annu. Rev. Neurosci. 12, 227-253); Thompson, R. B. and E. R. Jones (1993) Anal. Chem. 65, 730-734). Although ratiometric approaches minimize or avoid the artifacts associated with sample intensity measurements, its application has been restricted by the limited number of suitable commercially available fluorescent indicators.

Other researchers have shown that analyte concentration may be made proportional to changes in the fluorescence lifetime of a suitable indicator (Demas, J. N. and B. A. DeGraff (1994) in *Topics in Fluorescence Spectroscopy, Vol. 4: Probe Design and Chemical Sensing*, J. R. Lakowicz (Ed.) Plenum Press, NY., pp. 71-105; Lakowicz, J. R., H. Szmacinski and M. Karakelle (1993) Anal. Chim. Acta 272, 179-186; Lippitsch, M. E., J. Pusterhofer, M. J. P. Leiner and O. S. Wolfbeis (1988) Anal. Chim. Acta 205, 1-6; Thompson and Patchan (1993); Thompson, R. B. and M. W. Patchan (1994) Anal. Biochem. 227, 123-128). Consider, U.S. Pat. No. 5,464,587 (1995) to Lippitsch et al. which teaches the use of fluorescence decay time as the measurement variable for determining the activity of alkali metal ions in solution. Similarly, U.S. Pat. No. 5,545,517 (1996) to Thompson and Jones discloses a process for detecting metal ions in solution by measurement of changes in either the fluorescence lifetime or the ratio of fluorescence peak intensities. The present invention contrasts those described by Lippitsch (1995) and Thompson and Jones (1996), in teaching fluorescence polarization (anisotropy) as the measurement variable and not the use of fluorescence lifetime or ratios of intensities at different wavelengths. Further, although the changes in fluorescence emission noted by Thompson and Jones (1996) are significant, optimally a ligand whose lifetime decreases (unlike dansylamide) with binding to the metallo-enzyme complex would be preferred when anisotropy is measured.

The use of fluorescence polarization (anisotropy) to detect small molecules or drugs of abuse and therapeutics is well known (Dandliker. W. B., R. J. Kelly, J. Dandliker, J. Farquhar and J. Levin (1973) Immunochem. 10, 219-227). These early assays exploited the fact that small fluorescent molecules will rotate rapidly and exhibit low polarization, whereas large molecules will rotate more slowly and exhibit high polarization. Consider a small fluorescent labeled antigen (molecular weight$\leq$1000 daltons) unbound and in solution that has been excited with polarized light. It is likely that the excited fluorescent labeled antigen will rotate as the result of Brownian movement prior to emission because the rate of emission ($\sim 10^8$ sec$^{-1}$) is slower than the antigen's rotational rate ($\sim 10^{10}$ sec$^{-1}$). In turn, the change in rotation will effect the relative orientations of the absorption and emission dipoles of the fluorescent-labeled antigen, causing the emitted light to be depolarized. Conversely, if the fluorescent-labeled antigen was first bound by a much larger protein (e.g., an immunoglobulin (IgG) or enzyme) with a molecular weight on the order of 150,000 daltons, and then excited; its rotational rate will now largely reflect that of the slower moving larger molecule ($\sim 10^7$ sec$^{-1}$), and its fluorescence will likely be polarized. In a typical flourescence polarization competition assay, a known amount of fluorescent-labeled antigen and antibody are combined with a sample containing a quantity of unlabeled antigen whose concentration is unknown. The competition of the labeled and unlabeled antigen for the antibody is reflected in the measured fluorescence polarization which will be proportional to the fractional occupancy of the antibody binding sites. The fractional occupancy of these sites will be inversely proportional to the concentration of the unlabeled antigen present in the sample. In contrast to this assay format, one aspect of the present invention demonstrates for the first time the detection and quantitation of metal ions in solution by a homogeneous fluorescence polarization (anisotropy) assay that is based on proximity dependent quenching mechanisms and not simply to a change in the rotational correlation time of the fluorophore.

U.S. Pat. Nos. 5,495,850 and 5.515,864 (1996) to Zuckerman disclose the detection of oxygen by fluorescence polarization (anisotropy). In the methods described by Zuckerman, the lifetime of a fluorescent probe substance is quenched by molecular oxygen, the concentration of which is determined by measuring the fluorescence anisotropy of the probe. The quenching of the lifetime of the fluorescent probe results from the collision of the probe with oxygen, a well known quencher of fluorescence and phosphorescence. This process is sometimes referred to as collisional quenching and is usually interpreted in terms of the formation of a charge-transfer complex upon the collision of oxygen and the excited fluorophore (Lakowicz, J. R. (1983) *Principles of Fluorescence Spectroscopy*, New York, Plenum Press). The collisional quench mechanism disclosed in the Zuckerman patents differs from the proximity dependent quench mechanisms of the present invention as it depends on a dynamic event involving the collision and not the binding of a fluorophore with oxygen.

SUMMARY OF THE INVENTION

The present invention focuses on homogeneous photoluminescent polarization (anisotropy) assays for determining and quantifying metal ions in solution. In the preferred embodiments, the selective metal ion binding of macromolecules such as human carbonic anhydrase II variants (CA II)

are used to effect proximity dependent quenching of fluorescence with the binding of a metal ion to a "metal free" macromolecule. Further, this change is transduced by measuring fluorescence anisotropy which in turn is related to the concentration of the metal ion in solution. In all preferred embodiments, the changes in anisotropy can be simply related to the metal ion concentration of the solution. In the preferred embodiments, two methods are used to exploit the selectivity, affinity and flexibility of CA II in detecting metal ions in solution.

The first method relies upon metal-dependent binding of a fluorescent ligand to a macromolecule to effect a measurable change in the ligand's anisotropy. Binding of the ligand to the macromolecule is metal dependent with the change in anisotropy being proportional to the concentration of bound metal ions. No binding of the ligand to the macromolecule was found in the absence of metal ions. It is not necessary for the ligand to bind or coordinate to the metal and it also not necessary for the ligand to inhibit the activity of the macromolecule. This method of the invention has the steps of:

(1) disposing, in an aqueous solution containing a target metal ion species, a macromolecule for selective complexation with the target metal ion species; the macromolecule being able to reversibly bind the target metal ion species, resulting in the formation of a macromolecule-metal ion complex;

(2) disposing a fluorescent ligand species in the aqueous solution, wherein the fluorescent ligand reversibly binds to the macromolecule-metal ion complex;

(3) irradiating with plane polarized light, the fluorescent ligand species emitting polarized light in a measurably different manner when bound to the macromolecule-metal ion complex;

(4) monitoring the emission of the fluorescent ligand species to detect changes in the vector components of the fluorescence emission parallel (I∥) and perpendicular (I⊥) to the plane of polarization of the exciting light;

(5) calculating the fluorescence anisotropy from the vector components;

(6) relating the degree of anisotropy to the fraction of macromolecule-metal ion complexes, and to the binding affinity of said macromolecule, thereby determining metal ion concentration.

In the second method, a fluorescent label is first conjugated to the macromolecule which in turn is used to transduce the binding of metal ions, wherein the covalently bound fluorescent label exhibits changes in anisotropy proportional to the concentration of bound metal ions. This method of the invention has the steps of:

(1) disposing, in an aqueous solution containing a target metal ion species, a macromolecule having a fluorescent label covalently attached: wherein the target metal ion species reversibly binds to the labeled macromolecule forming a macromolecule-metal ion complex;

(2) irradiating with plane polarized light, the fluorescent label emitting polarized light in a measurably different manner with the formation of a macromolecule-metal ion complex;

(3) monitoring the emission of the fluorescent label to detect changes in the vector components parallel (I∥) and perpendicular (I⊥) to the plane of polarization of the exciting light;

(4) calculating the fluorescence anisotropy from the vector components;

(6) relating the degree of anisotropy to the fraction of macromolecule-metal ion complexes, and to the binding affinity of said macromolecule, thereby determining metal ion concentration.

The present invention minimizes problems common to methods based on simple fluorescence intensity measurements such as light scattering, photobleaching and variations in label concentrations, as anisotropy measurements are essentially independent of signal level. Further, the present invention is a homogeneous method, requiring no separation of assay components prior to the measurement of anisotropy. As a homogeneous method, there is no separation of free label from bound label which not only eliminates a separation step, but also minimizes the errors associated with the additional sample handling and testing that are required in a heterogeneous assay format.

Further, the present invention reduces the cost and complexity of metal ion analysis. It is an inexpensive and practical alternative for the quantitation of metal ions in solution in terms of not only instrument requirements but operator skill as well. The present ratiometric method is based on fluorescence polarization (anisotropy). It is essentially independent of total signal intensity and may easily be configured into battery operated devices with enough ruggedness to permit portability and field use given the numerous applications for metal ion analysis in environmental monitoring, industrial hygiene, and wastewater treatment. The homogeneous assay format of the present invention provides a response time that is limited only by the kinetics of the binding reaction, eliminating the need to consider equilibrium conditions for analysis.

DETAILED DESCRIPTION OF THE INVENTION

1. Definitions

For convenience, the meaning of certain terms and phrases employed in the specification, examples and appended claims are provided below.

"Ligand" broadly refers to molecules capable of binding to a macromolecule under certain conditions, such as in the presence of a metal ion bound to the same macromolecule. Such a ligand may be fluorescent and/or it may be an inhibitor of the macromolecule if the macromolecule is an enzyme.

"Macromolecule" as used herein, is meant to refer to a composition, which has a molecular weight of more than 5 kD. Macromolecules can be polypeptides, proteins, nucleic acids, polysaccharides, carbohydrates, lipids or other organic (carbon containing) or inorganic molecules.

"Photoluminescence," refers to any of a group of processes whereby a material is excited by radiation such as light, raised to an excited electronic or vibronic state, and subsequently re-emits that excitation energy as a photon of light. These processes include fluorescence, which denotes emission accompanying descent from an excited state with paired electrons (a "singlet" state) or unpaired electrons (a "triplet" state) to a lower state with the same multiplicity; a quantum-mechanically "allowed" transition. Photoluminescence also includes phosphorescence, which denotes emission accompanying descent from an excited triplet or singlet state to a lower state of different multiplicity; a quantum mechanically "forbidden" transition. Compared to "allowed" transitions, "forbidden" transitions are associated with relatively longer excited state lifetimes. Additionally, photoluminescent processes include emission from metal to ligand charge transfer excited states; the multiplicity of which is ill-defined or unknown. However, for all these photoluminescent processes polarization (anisotropy) measurements are well known in the art (Lakowicz (1983) and Eads, T. M., D. D. Thomas and R. H. Austin (1984) J. Mol. Biol. 179, 55-81). Thus we construe measurements of photoluminescence anisotropy described herein specifically to include measurements of phosphorescence anisotropy, fluorescence anisotropy and other photoluminescence from or to states of indeterminate multiplicity.

"Polarization", which is used interchangeable, with "anisotropy" refers to measurements of the polarization of fluorescence made according to the classic methods of Jablonski, Perrin, and Weber (see below for a fuller discussion). These two terms are simply related mathematically and measure the same phenomenon, but normalize the difference in light intensities measured through orthogonally oriented emission polarizers in a different fashion.

"Polarized light" refers to linearly polarized light, which is ideally what is employed in the art. However, as a practical matter elliptically-polarized light may also be used.

2. Theoretical Considerations

The principle of methods based on fluorescence polarization (anisotropy) is the observed partial polarization of the emission of a fluorescent probe (fluorophore) in solution when viewed perpendicular to the beam used for polarized excitation. Through photoselection, excitation with polarized light results in the selective absorption by only those fluorophore molecules which are appropriately oriented relative to the direction of the exciting beam. Further, if the selected absorbing fluorescent molecules are fixed and ordered in space, the polarization of the emitted light may be identical to that of the polarized excitation. However, other processes act to depolarize the emitted light. These processes include rotational diffusion and proximity-dependent quench mechanisms such as resonance energy transfer which act to reduce the fluorescence lifetime of the fluorophore. In turn, the degree of polarization will be inversely proportional to not only the speed of rotational diffusion or tumbling of the excited fluorophores in solution but also to the efficiency of energy transfer when it occurs.

The theory of fluorescence polarization (anisotropy) is well known (Lakowicz (1983); Weber, G. (1952) Biochem. J. 51, 145-155). In theory, the measurement of fluorescence polarization or anisotropy, refers to two measurements of the same phenomenon. Consider a sample that is excited with vertically polarized light with detection of the emitted light (fluorescence), generally at longer wavelength, through a polarizer that is oriented parallel to the direction of the polarized excitation. This will provide a measure of I∥, or the intensity of vertically polarized emission. If the polarizer is then oriented perpendicular to the direction of the polarized excitation, I⊥, the intensity of perpendicularly polarized light may be measured. Hence, polarization (P) and anisotropy (r) are defined by the equations:

$$P = \frac{I\| - I\perp}{I\| + I\perp} \quad (1)$$

$$r = \frac{I\| - I\perp}{I\| + 2I\perp}. \quad (2)$$

Polarization (P) and anisotropy (r) are readily interchangeable in accordance with the equations:

$$P = \frac{3r}{2+r} \quad (3)$$

$$r = \frac{2P}{3-P}. \quad (4)$$

Although the parameters are interchangeable and are functionally equivalent, theoretical expressions such as the Perrin equation (5) are much simpler in terms of anisotropy (r), and as a result, we consider only anisotropy (r) hereinafter.

$$r_0/r = 1 + (\tau/\phi) \quad (5)$$

The absorption of a photon by a ground state fluorophore will result in its radiative transition to an excited state. The fluorophore will subsequently return to the ground or a metastable state with the dissipation of energy. The de-excitation of the excited state can be effected by a number of competing processes which include fluorescence, radiationless transitions involving the dissipation of energy as heat, energy transfer and even transitions to metastable states. The lifetime of an excited state ($\tau$) is the average amount of time the fluorophore spends in the excited state prior to its return to the ground state. If fluorescence is the only means for de-excitation, the lifetime of the excited state is referred to as the intrinsic lifetime ($\tau_0$). Typically, the intrinsic lifetime of a molecule in the excited state varies inversely with the integrated area of its absorption band and is on the order of $10^{-9}$ to $10^{-8}$ seconds. However, since a molecule may de-excite by a number of competing pathways, the observed lifetime ($\tau$) is always smaller than ($\tau_o$).

Energy transfer often occurs by a dipole-dipole interaction (Förster, T. (1948) Ann. Phys. 2, 55-75). The rate of Forster energy transfer ($K_T$) is a function of the distance between the centers of the dipole oscillators of the donor (D) and acceptor (R); the refractive index of the medium ($\eta$), the overlap integral (J) of the fluorescence spectrum of the donor (D) and the absorption spectrum of the acceptor (A); the rate of emission of the donor (D) in the absence of acceptor (A) ($\lambda_d$) and the relative orientation of the electric dipole oscillators ($\kappa^2$):

$$K_T = 8.7 \times 10^{23} (r^{-6} J \kappa^2 \eta^{-4} \lambda_d) \text{sec}^{-1} \quad (6)$$

The rate of Förster energy transfer may be simply expressed in terms of the Förster distance ($R_0$) and the lifetime of the donor ($\tau_D$):

$$K_T = 1/\tau_D (R_o/R)^6 \quad (7)$$

where $R_o$ is the critical distance. The critical distance ($R_o$) is defined as the distance between the donor and acceptor at which the rate of dipole-dipole or resonance energy transfer equals the rate of fluorescence emission. From this equation, it is evident that the rate of energy transfer will fall off sharply with increasing distance between the donor and acceptor.

In the Perrin equation (5), r is the actual or observed anisotropy; $r_0$ is the limiting anisotropy or the anisotropy one would observe in the absence of any depolarizing processes such as rotational diffusion; $\tau$ is the fluorescence lifetime and $\phi$ is the rotational correlation time. It is evident from this equation that the actual anisotropy of the sample will be inversely proportional to the fluorescence lifetime. It should also be apparent that if the rotational correlation time increases relative to the fluorescence lifetime, the difference between r and $r_0$ will decrease. For an example, consider the case where the rotational time is the same as the lifetime of the fluorescent label. Let's assume we have a roughly spherical macromolecule with a 30 kD molecular weight with a fluorescent label that is rigidly attached (e.g., no segmental motion) giving a rotational relaxation time ($\phi$) of 15 nsec, a fluorescence lifetime of 15 nsec and an $r_0$ of 0.4. Based on these parameters, one may expect to observe an anisotropy of 0.2. Now, if the quantum yield of the fluorescent label changes upon the reversible binding of a metal ion to the macromolecule at a particular site, resulting in 50% quenching and a concomitant 50% reduction in the fluorescence lifetime; then the anisotropy of the metal-bound macromolecule would be 0.27. However, in a solution with only partial occupancy of binding sites with metal ions, the observed anisotropy (r) would reflect contributions from the anisotropies of both the metal-free ($r_f$) and "metallo" ($r_b$) forms of the macromolecule. The fractional saturation of the sites with metal ions ($f_b$) is a simple function:

$$f_b = (r-r_f)/[(r_b-r)R+(r-r_f)] \quad (8)$$

where R is the quantum yield ratio of the "metallo" to the metal-free forms ($R=q_b/q_f$).

Figure 1:
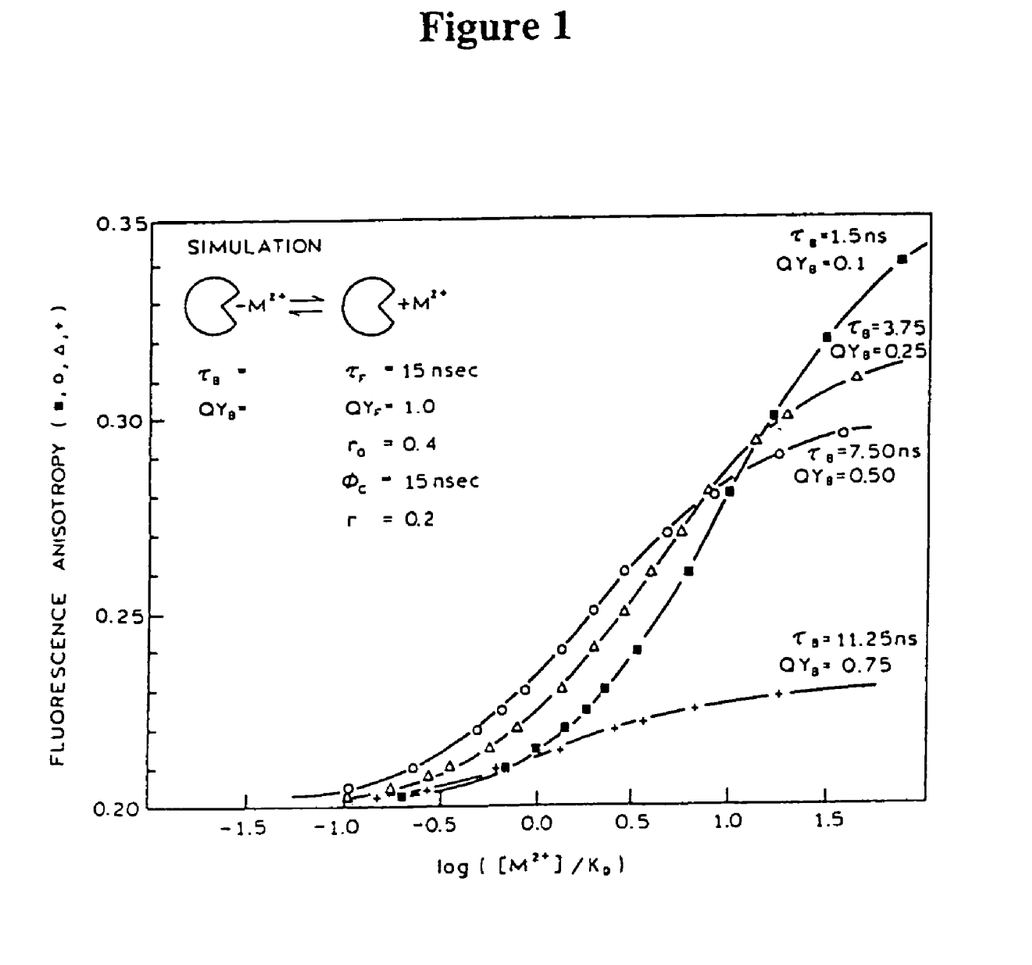
FIG. 1 Simulated anisotropy of a macromolecule-bound fluorophore partially quenched by a metal ion. A macromolecule having a rotational correlation time $\phi_c$=15 nsec with a tightly bound bluorescent label having a lifetime $\tau$=15 nsec reversidly binds a metal ion which quenches the label emission by 25% (+), 50% (o), 75% (■), or 90% (Δ). The fluorescence anisotropy is depicted as a function of the logarithm of the metal ion concentration, expressed as the ratio of the metal ion concentration to its $K_D$.

The concentration of the metal ion can be simply determined from the law of mass action if both the fractional saturation and the affinity constant ($K_D$) of the metal ion for the macromolecule are known. Simulated plots of anisotropy as a function of metal ion concentration for different degrees of quenching are shown in FIG. 1. The pronounced asymmetry of the curves at higher degrees of quenching are due to the disproportionately small contribution of the more highly quenched bound forms to the total emission. Even though a higher degree of quenching results in an increased span of anisotropy between the free and bound forms, the true dynamic range of the measurement is little improved because the highly quenched form is so dim.

The above example presents an idealized case since it is likely that the fluorescent label will exhibit some segmental motion independent of the macromolecule. Given that the fluorophore has a lifetime similar to the rotational time of the macromolecule, a significant rate and extent of segmental motion would likely effect a much lower anisotropy as the rotational correlation times of molecules, as small as typical fluorescent labels, are usually less than one nanosecond. Even if the lifetime of the fluorescent label was longer (i.e., a few nanoseconds), the anisotropy would still be low, but under favorable conditions one might observe a usable increase in anisotropy if the lifetime was reduced. Unless the fluorescent label is attached by a "linker arm" containing several bonds, the likelihood of segmental motion is difficult to predict. However, it may be measured by time-resolved anisotropy or its frequency-domain analog. differential polarized phase fluorometry. Note that if segmental motion can be conferred and controlled, it becomes possible to use labels with much shorter lifetimes than are necessary with macromolecules having longer correlation times.

3. Macromolecules, Fluorescent Labels and Metal Ions

Figure 2:
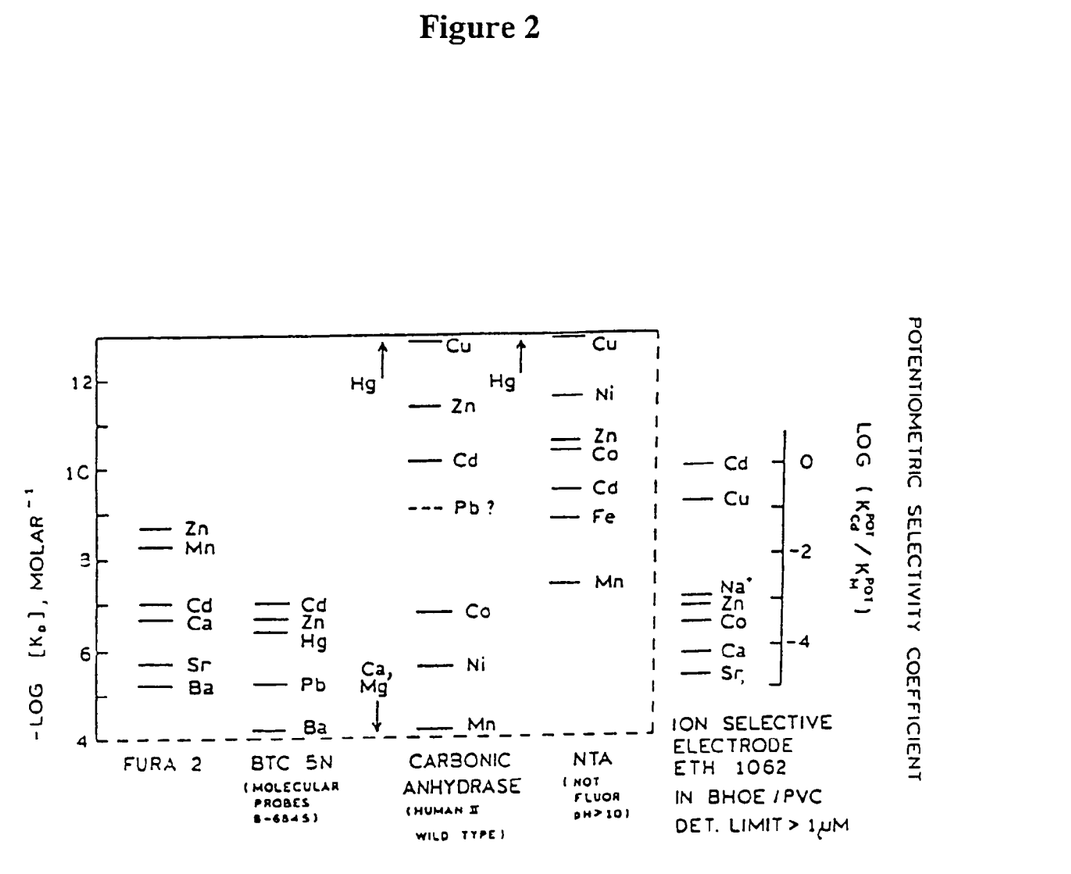
FIG. 2 Selectivity, sensitivity of transducer molecules. Binding constants for divalent metal ions are depicted for the metallo-fluorescent indicators Fura-2 and BTC-5N, wild type human carbonic anhydrase II, and the chelator, nitrilotriacetic acid at pH >10. Also depicted are the selectivity coefficients for divalent cations and $Na^+$ for a cadmium-selective electrode. Fura-2 and BTC-5N are commercially available from Molecular Probes, Eugene, Oreg.

Several embodiments of the present invention rely on the binding of metal ions to a variant of the enzyme, carbonic anhydrase II (CA II). This zinc-containing metallo-enzyme (MW=30 kD) normally catalyses the reversible reaction:

$$CO_2 + H_2O \leftrightarrows HCO_3^- + H^+ \quad (1)$$

as well as the hydrolysis of esters and the hydration of aldehydes (Moratal, J., M. J. Martinez-Ferrer, A. Donaire, J. Castells, J. Salgado and H. Jimenez (1991) J. Chem. Soc., Dalton Trans. 3393-3399). For some time, we have exploited the selectivity, affinity and flexibility of this metallo-enzyme in transducing the concentration of metal ions as a change in fluorescence. FIG. 2 depicts the selectivity of this enzyme for divalent cations with other metallo-fluorescent indicators and an ion selective electrode. Note that in comparison to the well-known Ca(H) indicator Fura-2 (Tsien, R. Y. and T. Pozzan (1989) in *Methods in Enzytnology Vol. 172. Bioineinbranes Part S. S.* Fleischer and B. Fleischer (Eds.), Academic Press, New York, pp 230-262) and the newly developed heavy metal indicator BTC-5N, CA II binds Zn (II) three to five orders of magnitude more tightly, which generally equates to improved sensitivity. Although the chelator, nitrilotriacetate (NTA) exhibits binding affinity (at pH 10) similar to that of the enzyme, it is completely non-fluorescent and clearly less selective amongst transition metals than CA II. It is also of interest to note the greater dispersion in the binding constants of the divalent cations Zn (II), Cd (H), Co (II), Ni (II) and Mn (II) with CA II as compared to Fura-2 and BTC-5N. By comparison, the cadmium ion-selective electrode (Ammann, D., W. E. Morf, P. Anker, P. C. Meier, E. Pretsch and W. Simon (1983) Ion-Selective Electrode Rev. 5, 3-92) is clearly inferior in terms of its sensitivity and selectivity between the divalent cations.

The use of wild type or variants of human carbonic anhydrase II is taught as the best mode. Alternative embodiments within the scope of this invention include, but are not limited to other human carbonic anhydrase isozymes; carbonic anhydrases from other species such as cow and spinach; other metalloenzymes including alkaline phosphatases, leucine aminopeptidases, carboxypeptidases, laccases, azurins, and ureases from diverse species; other metallo-enzymes for which inhibitor binding is metal-dependent or which bind metals exhibiting charge transfer d-d absorption bands, mutants and variants of the above enzymes; biological, biomimetic, organic and inorganic polymers; metal-binding reagents, nucleic acids, polysaccharides, carbohydrates and nonbiological polymers are also anticipated as potentially useful by this disclosure.

Several embodiments of the present invention rely on the fluorescent labels dansyl aziridine, 4-chloro-7-sulfobenzofuran (SBF), 7-fluorobenz-2-oxa-1,3-diazole-4-sulfonamide (ABD-F) and nitrobenzoxadiazolyl. Alternative embodiments within the scope of this invention include, but are not limited to the following fluorescent labels: fluorescein isothiocyanate, rhodamine iodoacetamide, CY3 iodoacetamide and Green Fluorescent Protein. It should be understood that many of the fluorescent labels commercially available (Haugland, R. P. (1996) *Handbook of Fluorescent Probes and Research Chemicals, 6th Edition*, Molecular Probes, Eugene, Oreg.), other fluorescent labels disclosed in the literature, as well as the intrinsic tyrosyl and tryptophanyl fluorescence of the protein, and phosphorescent labels are feasible and anticipated by this disclosure.

Embodiments of the present invention include but are not limited to determining and quantifying Zn(II) and Cu(II) metal ions in solution. Co(II), Cd(II), Ni(II), Hg(II), Fe(II), Mn(II), Pb(II) and other metal ions which are known to bind to carbonic anhydrases, proteins and macromolecules with greater or lesser affinity and which quench fluorescence themselves or promote the binding of inhibitors which quench the fluorescence and are also feasible and anticipated by this disclosure.

Embodiments of the present invention include but are not limited to the following photoluminescent ligand species: 4-aminosulfonyl [1-(4-N-(5-fluoresceinylthioureido)butyl)] benzamide, ABD-F (7-fluorobenz-2-oxa-1,3-diazole-4-sulfonamide):β-Mercaptoethanol Adduct, (i.e., 4-(2-hydroxyethylthio)-7-aminosulfonyl-2,1,3-benzoxadiazole), dansylamide, hydroxynapthalenesulphonamide, 2-(3 methoxy-4-ethoxyphenyl)-4-chloroquinoline-6-sulfonamide, N-(1-anthracenyl)-4-sulfonamido-benzenesulfonamide, ethyl-2-(4-sulfonamidophenyl)-4-hydroxyquinoline-6-carboxylate and N-(N'-(4'sulfamoylglutaranilyamidoethyl))-4-amino-3,6-disulfo-1,8-naphthalimide.

Figure 3:
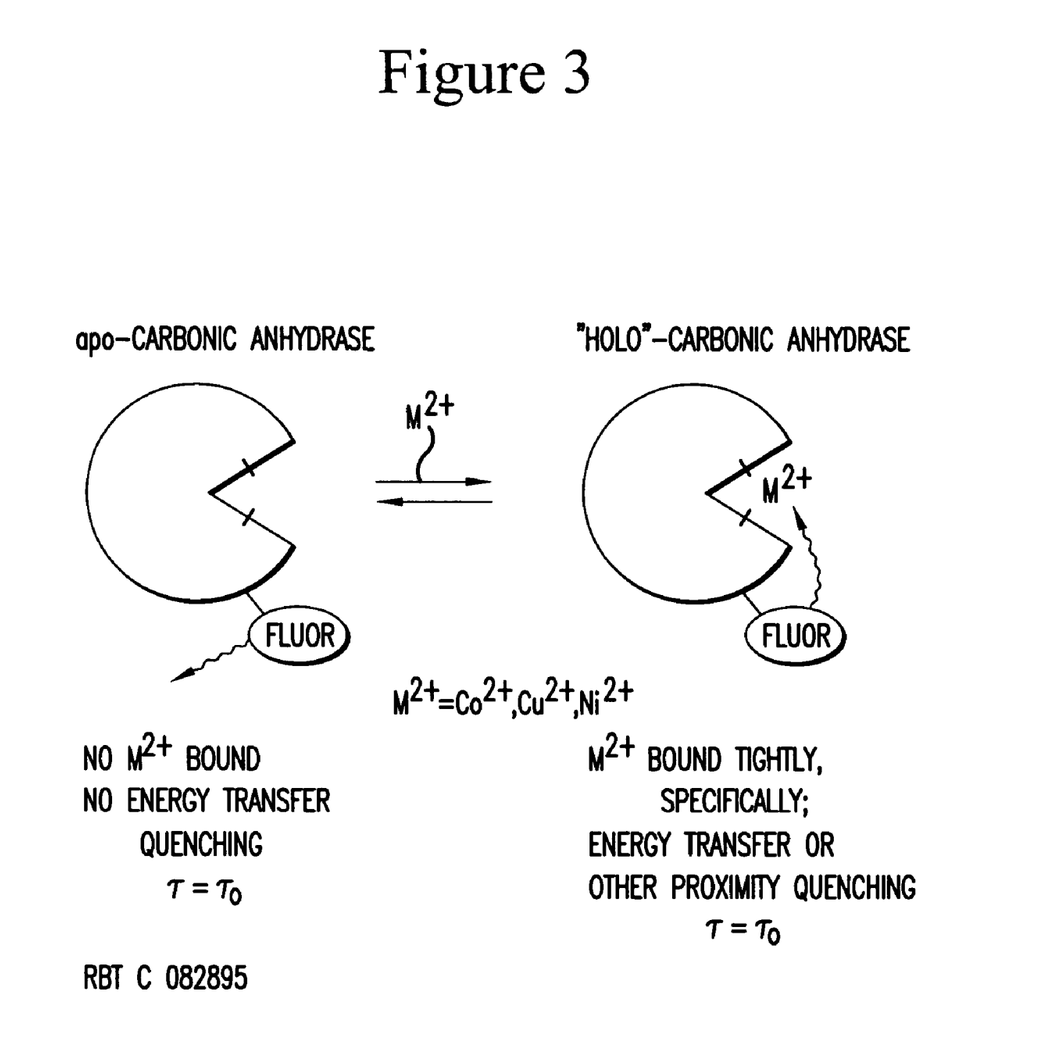
FIG. 3 Transduction scheme for anisotropic metal ion detection based on fluorescence energy transfer or other proximity quenching mechanism.

4. Metal Ion Detection by Anisotropy Using a Photoluminescent Labeled Macromolecule The metal ions, Ni (II), Co(II), and Cu(II) exhibit weak d-d absorbance bands which can undergo characteristic changes upon binding to a macromolecule (e.g., CA II) (Lindskog, S., L. E. Henderson, K. K. Kannan, A. Liljas, P. O. Nyman and B. Strandberg (1971) in *The Enzymes, Vol. 5, Third Edition*. P. D. Boyer (Ed.), Academic Press, New York, pp 587-665). Such absorbing species can serve as energy transfer acceptors (A) for a fluorescent donor (D) with suitable position, orientation, and spectral overlap, and thus may transduce their binding by the macromolecule as a change in the fluorescence intensity, lifetime or anisotropy of the donor (D). The transduction scheme for anisotropy metal ion detection based on fluorescence energy transfer or an alternative proximity quenching mechanism is depicted in FIG. 3, wherein the divalent metal ion ($M^{2+}$) acts as the energy transfer acceptor (A) and the fluor acts as the fluorescent energy donor (D). While the results with this method are consistent with the theory of resonance energy transfer (Förster (1948)), this does not preclude the existence and contribution by other proximity-dependent quenching processes. Other metals that do not absorb light but bind to the macromolecule may also be transduced in this manner. Such assays are well known in the art.

In the case of homogeneous energy transfer-based transduction, binding of the metal ion results in quenching, with a commensurate reduction in quantum yield. Again, assuming suitable position, orientation, and spectral overlap between the D and A, a significant reduction in lifetime may be achieved with a correspondingly reduced quantum yield. When energy transfer is very efficient, the quenched form would contribute very little to total emission except near saturation and may therefore jeopardize the collection of accurate data. Similarly, if energy transfer in the bound form is very modest, the lifetime change and therefore the change in anisotropy will be small as well and more difficult to quantitate. Qualitatively, this suggests that there is some suitable middle ground of energy transfer efficiency that will result in an optimal response (Thompson et al., 1996). By using site-directed mutants of CA II in the present invention, we are able to adjust the position of a fluorescent label at particular sites on the exterior of CA II, providing an optimal response for a homogeneous assay as compared to what we would have been able to achieve with nonspecific labeling approaches. Specifically, we used site-directed mutagenesis to create CA H variants with cysteine residues at desired points for selective derivatization with suitable labels. Desirable positions for the donor with respect to the acceptor may be predicted based on the Förster theory described above.

Studies have been performed in our laboratory using fluorescent labeled site-directed mutants of apo-CA II to recognize the binding of Cu (II), Co (II), Cd (II), Hg (II), Ni (II) and Zn (II) to the active site. Binding is transduced as a change in fluorescence lifetime or anisotropy due to proximity-dependent quenching by Förster or other mechanisms. The binding of Co (II) to a CY-3 labeled apo-N67C variant of CA II resulted in a drop in the mean lifetime of CY-3 by approximately 60%. If the lifetime change is measured by phase fluorometry, the measured phase angle and modulation at some suitable frequency will be a single-valued function of the fractional occupancy of the binding sites which may in turn be simply related to the metal ion concentration of the solution (U.S. patent application Ser. No. 08/736,904). For a short-lifetime probe such as CY-3 with a mean lifetime of approximately 1.6 nsec, attached to a 30 kD CA II molecule (rotational correlation time 15 nsec (Chen, R. F. and J. C. Kemohan (1967) J. Biol. Chem. 242, 5813-5823), a reduction in lifetime will result in a negligible increase in anisotropy. In contrast, a label with a longer lifetime will show a significant increase in anisotropy provided: (1) its lifetime approximates the rotational correlation time of CA II; and (2) it is quenched by a proximity or energy transfer dependent mechanism. Of course, other metal-label interactions can conceivably result in an increase in lifetime, and a concomitant decrease in polarization. Hence, by using an array of site-directed cysteine variants of the wild-type protein and assorted thiol-specific fluorescent labels, suitable combinations were found which would exhibit specific, metal-dependent changes in fluorescence polarization. Significant changes in anisotropy and intensity were found when dansylaziridine labeled variants of CA II were used to detect Cu (II); when 4-chloro-7-sulfobenzofurazan (SBF) labeled variants of CA II were used to detect Zn (II); when 7-fluorobenz-2-oxa-1,3-diazole-4-sulfonamide (ABD-F) labeled variants of H64C of CA II were used to detect Zn (II).

5. Metal Ion Detection by Anisotropy Using a Photoluminescent Ligand

Figure 4:
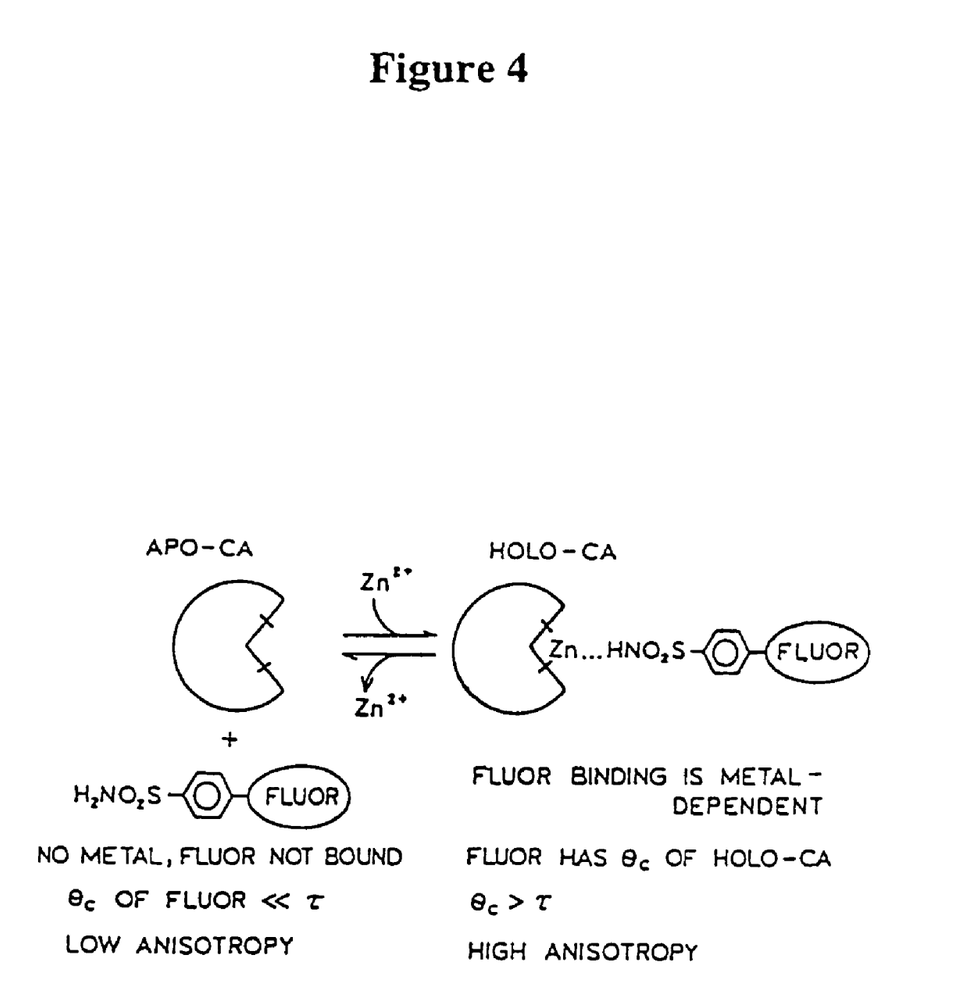
FIG. 4 Transduction scheme for anisotropic metal ion detection using a photoluminescent ligand is depicted.

The selective binding of a photoluminescent ligand to a CA II-metal ion complex is used to transduce the concentration of metal ions. This method exploits the change in anisotropy of a photoluminescent ligand between its free and enzyme-bound states. For example, consider a photoluminescent ligand that does not bind to apo-CA II and due to its low (0.1 nsec) rotational correlation time exhibits little or no anisotropy. In contrast, when a metal binds to the active site of the enzyme, the ligand binding is enhanced and its anisotropy increases due to the slower rotation (correlation time of approximately 15 nsec) of the CA II molecule. Anisotropy will therefore be proportional to the fractional occupancy of the metal binding sites of CA II by the metal ion, which in turn is proportional to its concentration in solution. However, one drawback of this approach is that it requires both the ligand concentration and the concentration of CA II to be at or near the indicator $K_D$, for optimal sensitivity. The transduction scheme for this method of metal ion detection using anisotropy is depicted in FIG. 4 and was described in detail by Elbaum et al. (1996) (Elbaum, D., S., Nair, M. Patchan, R. Thompson and D. Christianson (1996) J. Am. Chem. Soc. 118, 8381-8387).

EXAMPLES

The following examples are provided for illustrative purposes only, and are not intended to limit the scope of the present invention. All CA II variants and wild types were provided as a generous gift from Professor Carol Fierke, Department of Biochemistry, Duke University Medical Center, Durham, N.C.

1. Anisotropy Determination of Zinc(II) in Solution with apo-L198C Variant of CA II-SBF Conjugate The principle of energy transfer biosensing of a metal ion (Zn(II)) without a separate inhibitor by measuring changes in fluorescence anisotropy is demonstrated. The recombinant human carbonic anhydrase II variant, L198C was produced by site-directed mutagenesis, expressed in *Escherichia coli* strain BL21LDE3 and purified as previously described (Krebs et al., 1993), the leucine at position 198 being replaced with a cysteine. The reactive cysteine residue of LC198C was conjugated with 4-chloro-7-sulfobenzofurazan (SBF) (Fluka, Ronkonoma, N.Y.; Cat. No. 26375). SBF is water soluble and highly specific for thiol groups in aqueous media (Andrews, J., P. Ghosh, B. Ternal and M. Whitehouse (1982) Arch. Biochem. Biophys. 214, 386-396). Prior to conjugation, L198C was dialyzed overnight into 1 M tris, pH 8.6 and then reacted with dithiothreitol (DTT) for 4 hours. SBF in tris, pH 8.6 was then added at 2 times the total thiol content of the solution. The reaction solution was then allowed to incubate for one hour at room temperature in the dark with stirring. The reaction was stopped by the addition of ten-fold molar excess of β-mercaptoethanol over the molar content of SBF. Unreacted SBF was removed by gel filtraion using a PD10 column (Pharmacia Biotech, Uppssla. Sweden; Cat. No. 51-5107-00-AB). Zinc was removed from the conjugated L198C-SBF by treatment with aqueous dipicolinate as previously described (Hunt, J. B., M.-J. Rhee and C. B. Storm (1977) Anal. Biochem. 79, 614-617). Subsequent contamination of apo-L198C with metal ions was minimized by storage in metal-free plastic tubes and using buffers pretreated with a chelating resin. L198C-SBF was dialyzed overnight into 50 mM Na HEPES buffer, pH 7.3, 150 mM sodium sulfate.

Figure 5:
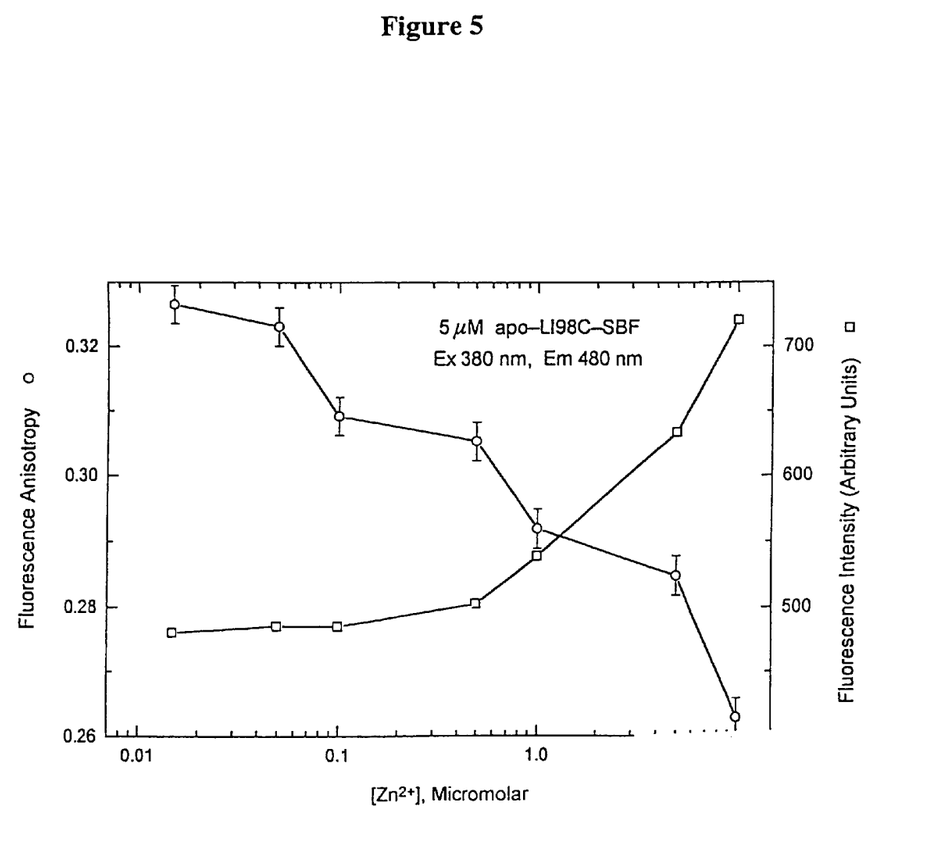
FIG. 5 The relative fluorescence intensities and the anisotropies at 480 nm for a 5 μM concentration of the conjugated CA H variant apo-L198C-SBF as a function of Zn(II) concentration.

Fluorescence anisotropies were measured on an SLM 8000c steady-state fluorometer with a xenon lamp for excitation through the courtesy of J. R. Lakowicz and the Center for Fluorescence Spectroscopy, Department of Biological Chemistry, University of Maryland at Baltimore, Baltimore, Md. Response to Zn(II) was calibrated in 50 mm Na HEPES buffer pH 7.3, 150 mM sodium sulfate with varying concentrations of zinc sulfate by fluorescence intensity and anisotropy with excitation at 380 nanometers and emission at 480 nanometers with 8 nanometer slits. FIG. 5 shows both the relative fluorescence intensities and the anisotropies at 480 nm for 5 μM apo-L198C-SBF as a function of Zn(II) concentration.

2. Anisotropy Determination of Copper(II) in Solution with apo-V143C Variant of CA II-Dansylaziridine Conjugate The principle of energy transfer biosensing of a metal ion (Cu(II)) without a separate inhibitor by measuring changes in fluorescence anisotropy is demonstrated. Variants of recombinant human carbonic anhydrase II (V143C) were produced as described above. The reactive cysteine residue of V143C was conjugated with dansylaziridine (Molecular Probes, Eugene, Oreg.; Cat. No. D-151). Conjugation was accomplished by treatment with fifty-fold molar excess of dansylaziridine over carbonic anhydrase at pH 8.2 for three hours at room temperature in the dark with stirring. The reaction was stopped by the addition of ten-fold molar excess of β-mercaptoethanol over the molar concentration of dansylaziridine; unconjugated dansylaziridine was removed by gel filtration. This technique is a modification of the procedure described by Pikuleva et. al. (1991) (Pikuleva, I., I. Turko, T. Adamovich and V. Chashchin (1991) Mol. Immunol. 28, 311-318). Zinc was removed from the derivatized enzyme by treatment with aqueous dipicolinate as described above. All subsequent handling and storage of the enzyme was in plastic, and buffers treated with chelating resin to prevent unwanted metal ion contamination. The labeling efficiency was determined by absorbance using the known visible extinction coefficient of dansylaziridine (Haugland (1996)) together with a Bradford protein assay (Pierce, Rockford, Ill.; Cat. No. 23236) using human carbonic anhydrase II as a standard.

In view of the well known difficulties in preparing solutions with accurate and reproducible low free metal ion concentrations, a series of metal ion buffers were prepared using Cu (II), nitrilotriacetic acid (NTA) and MOPS. NTA has a relatively high affinity for Cu (II) near neutral pH, and consequently a very high proportion of added Cu (II) will be bound by the NTA; variations in the free Cu (II) concentration due to binding by other ligands or contamination from other sources are counteracted by the release or uptake of Cu (II) by the NTA, thereby buffering the metal ion concentration. The concentration of Cu (II) unbound at a particular pH is readily calculable from the known stability constants of the NTA and the pKa's of NTA's ionizable groups (Smith, R. and A. E. Martell (1973) National Institute of Standards and Technology, U.S. Department of Commerce, Gaithersburg, Md.). Free Cu (II) was buffered with 5-15 mM NTA, pH at 7.0 with 10 mM MOPS.

Figure 6:
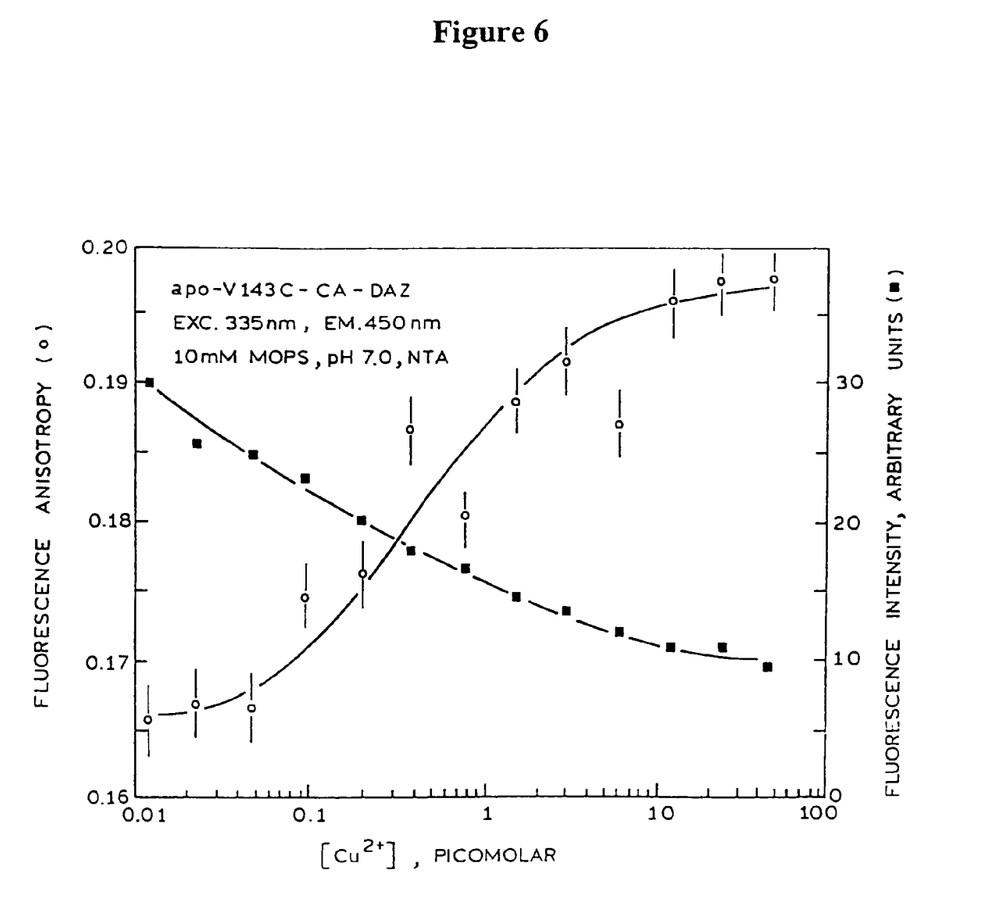
FIG. 6 The relative fluorescence intensities and the anisotropies at 450 nm for a 500 nM concentration of the conjugated CA II variant apo-V143C-dansyl aziridine as a function of Cu(II) concentration.

Absorbance spectra were recorded using a Hewlett/Packard 6452A spectrophotometer. Anisotropies were obtained as above with excitation at 335 nanometers and emission at 450 nanometers with 8 nanometer slits. FIG. 6 shows the relative fluorescence intensities and the anisotropies for 500 nM apo-V 143C-dansylaziridine as a function of Cu(II) concentration. When Cu(II) is present in the active site of CA II, it will be in close proximity to the label, dansylaziridine. Due to the overlap in the emission wavelengths of dansylaziridine and the wavelenghts of Cu(II) absorption, energy transfer between the label and Cu(II) occurs such that the intensity and lifetime of dansylaziridine are diminished.

Figure 7:
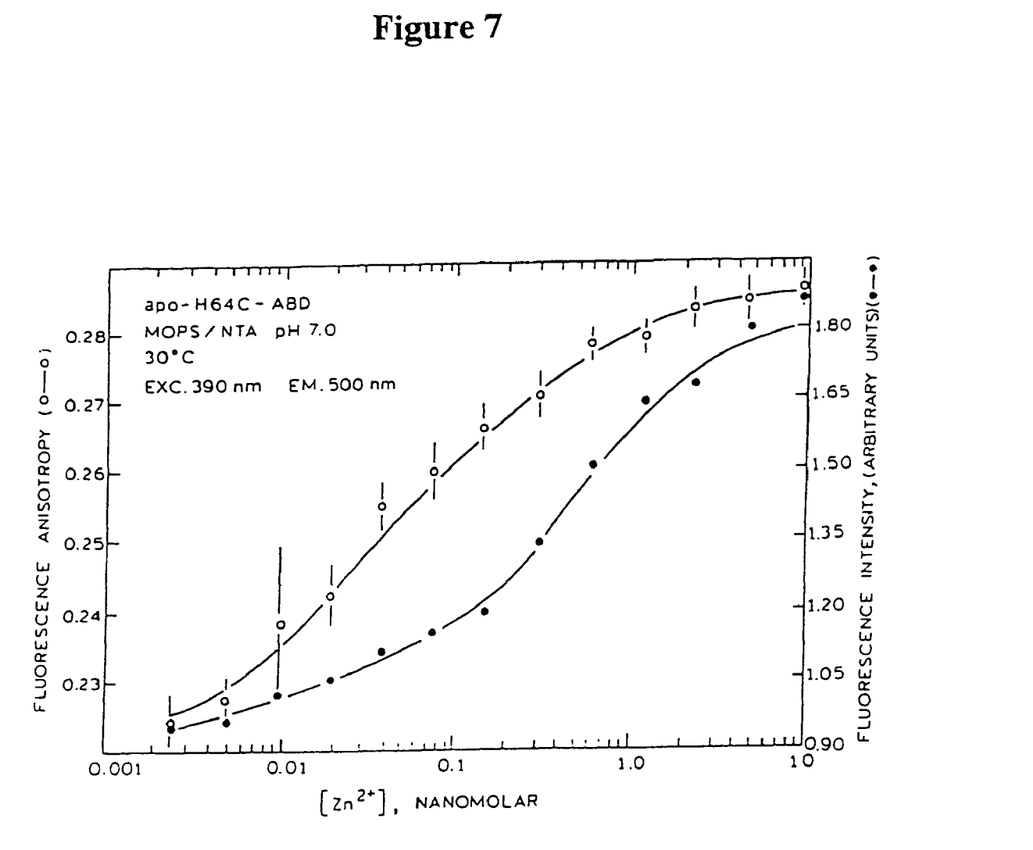
FIG. 7 The relative fluorescence intensities and the anisotropies for apo-H64C-ABD-F as a function of Zn(II) concentration.

3. Anisotropy Determination of Zinc (II) in Solution with apo-H64C CA II-ABD-F Conjugate Two milligrams of a variant form of human apo-carbonic anhydrase II with the histidinyl residue at position 64 substituted with cysteine ($H_{64}C$ CA II) was conjugated with tenfold molar excess 7-fluorobenz-2-oxa-1,3-diazole-4-sulfonamide (ABD-F) (Molecular Probes. Eugene. Oreg.: Cat. No. F-6053; CAS Registry No. 91366-65-3) in 100 mM borate pH 9.0, 1.0 mM NaCl at room temperature for 4-6 hours. The conjugate was isolated by centrifugal dialysis. Fluorescence anisotropy was measured on a Spectronics AB-2 fluorimeter with excitation at 390 nanometers and emission at 500 nanometers with 8 nanometer slits. Solutions for calibration having low free zinc concentrations were prepared as described above using NTA as a metal ion buffer, pH at 7.0 with MOPS. Zinc was determined by mixing 1.5 μmolar H64C CA-ABD-F with the sample in aqueous solution and measuring intensity and anisotropy. FIG. 7 shows the relative fluorescence intensities and the anisotropies for apo-$H_{64}C$-ABD-F as a function of Zn(II) concentration.

4. Anisotropy Determination of Zinc (II) in Solution with Wild Type apo-CA II-ABD-F: β-Mercaptoethanol Adduct (ABD-M)

Figure 8:
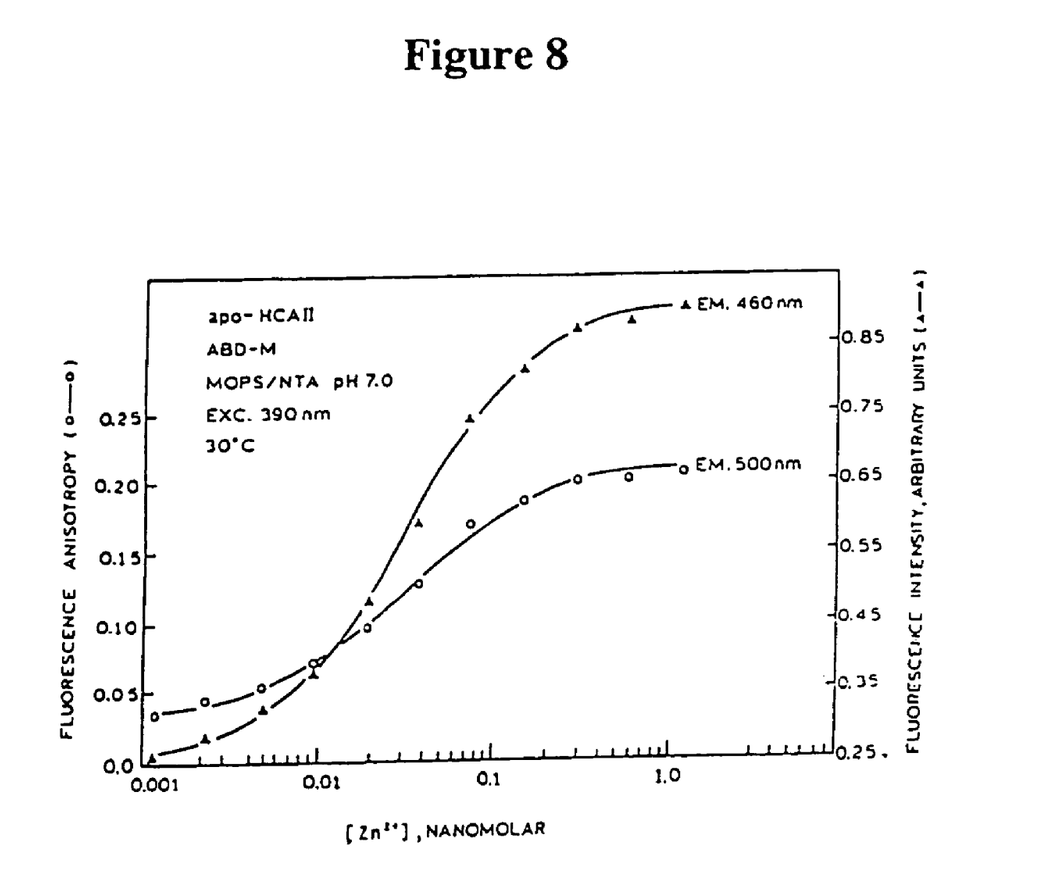
FIG. 8 The relative fluorescence intensities and the anisotropies for ABD-F:β-Mercaptoethanol Adduct and wild type apo-H64C as a function of Zn(II) concentration.

ABD-F (2 mg) was coupled with beta-mercaptoethanol (five-fold molar excess) in dimethylformamide (DMF) (Aldrich; Cat. No. 27,054-7) for four hours at 37° C., yielding a yellow compound which fluoresced a bright greenish yellow in methanol-water mixture (see J. L. Andrews et al. (1982) for details on a similar compound). The estimated extinction coefficient of the ABD-F:mercaptoethanol adduct (ABD-M) was 14,000 $M^{-1}$ $cm^{-1}$ near neutral pH in water. Zinc was removed from human carbonic anhydrase II as described above. The anisotropy and intensity response to Zn(II) was calibrated by mixing 2 micromolar ABD-M with 2.5 micromolar human apo-carbonic anhydrase II at 30° C. in a pH 7.0, 15 mM MOPS 15 mM nitrilotriacetic acid (NTA) buffer with differing amounts of zinc sulfate added. As above, the NTA serves to buffer the zinc ion concentration in a method well known to the art such that very low concentrations of free zinc ion in the solution may be reproducibly prepared. Fluorescence anisotropy was measured on a Spectronics AB-2 fluorimeter with excitation at 390 nanometers and emission at 500 nanometers with 8 nanometer slits, and emission intensity at 460 nanometers with the same slits. FIG. 8 shows the relative fluorescence intensities and the anisotropies for ABD-F:β-Mercaptoethanol Adduct (ABD-M) and wild type apo-CA II as a function of Zn(II) concentration.

5. Anisotropy Determination of Zinc(II) in Solution Using CA II and a Fluorescein-Based Arylsulfonamide Ligand The principle of biosensing of a metal ion Zn(II) which does not depend on metal-dependent changes in the fluorescence spectra of the label are demonstrated by measuring the fluorescence anisotropy of a fluorescein-based arylsulfonamide probe. In the free state, the probe has a low rotational correlation time and exhibits a low anisotropy. When bound to a metallo-CA II complex, anisotropy increases due to the slower rotational correlation time of the CA II molecule.

Figure 9:
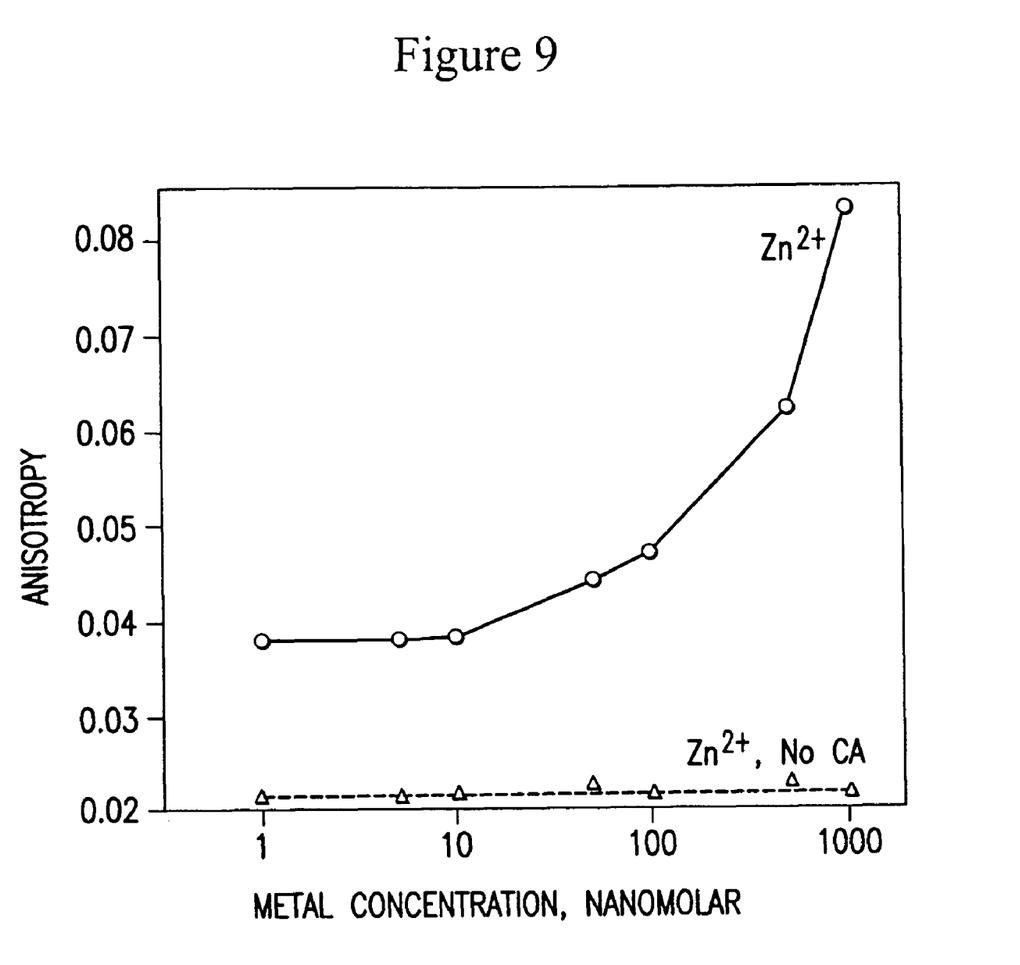
FIG. 9 The fluorescence anisotropy of 1 μM fluorescent ligand as a function of Zn(II) concentration in the absence and presence of 1 μM apo-CA II.

Reagents were prepared as previously described (Elbaum et al. (1996)). Fluorescence anisotropies were measured on an SLM 8000c steady state fluorometer with a xenon lamp for excitation. Excitation was at 488 nm; emission was detected at 520 nm and a KV500 emission filter. Blank spectra indicated negligible background fluorescence and no apparent scattered excitation. Under these conditions, the accuracy and precision of the anisotropy measurements were ±0.003 or better. From equation (8), the fraction of the fluorescence inhibitor bound is a simple function of the anisotropies of the free and bound states, the ratio of their quantum yields, and the measured anisotropy at some intermediate saturation. The apparent quantum yield changed negligibly upon binding to CA II. In contrast to the above examples, recombinant wild-type CA 11 was used instead of a site-directed mutant. Apo-CA II was prepared essentially as described above. The fluorescence anisotropy of 1 μM fluorescent inhibitor as a function of Zn(II) concentration in the absence and presence of 1 μM apo-CA II is depicted in FIG. 9.

The analytic methods disclosed in the instant application provide at least the advantage that divalent metal ions can be analyzed in a quantitative fashion at very low, i.e. sub-nanomolar, concentrations. The inventive methods also provide an assay that has a broad dynamic range for quantitation of the analyte. These advantages spring from compositions according to the invention that comprise a metal binding protein and a photoluminescent compound (fluorophore) as described herein.

One advantage that derives from the compositions of the invention is the ability to utilize energy transfer from a fluorophore to a protein bound metal ion, thereby maximizing the change in anisotropy that can be observed upon metal binding. This method is made available by the combination of the fluorophore with the metal-ion binding protein.

The above advantage is optimized by site-directed covalent attachment of the fluorophore to the protein as described herein. The optimization that is derived from these embodiments of the invention arises from optimization of the apparent change in lifetime due to Forster energy transfer from the covalently attached fluorophore to the protein-bound metal ion (thereby maximizing the change in anisotropy, and thus sensitivity). The covalently-bound fluorophore (e.g., as illustrated in FIG. 3) may be positioned relatively close by the metal ion binding site at a distance which may be predicted by Forster theory (Thompson, et al., J. Biomed. Opt. 1,136 (1996), hereby incorporated by reference).

Site-specific introduction of a cysteinyl residue on the surface of the metal ion-binding protein, (for example at position 198 of carbonic anhydrase as in FIG. 5, or at position 143 of carbonic anhydrase as in FIG. 6) which cysteinyl residue may be selectively, covalently labeled with fluorescent labels using techniques well known in the art, such that the label is attached at a predetermined place on the protein, and nowhere else. Such site-directed attachment of the photoluminescent molecule provides an advantage over merely randomly attaching a fluorophore to the protein (for instance, to apocarbonic anhydrase by reaction of a covalent fluorescent label such as fluorescein isothiocyanate (FITC), a technique well known in the literature), because random attachment is not likely to yield a useful change in anisotropy. This is because the lifetime of the excited state of the fluorophore may not change significantly because it may be too far away to be significantly quenched by the bound metal ion. Indeed the non-site directed labeling process, which may take place at any, all, or some fraction of several residues on the surface of the metal ion-binding protein, (e.g lysines at the surface of apocarbonic anhydrase) is essentially random and so usually results in a derivatized protein that does not provide any change in the lifetime of the excited fluorophore.

The achievement of a sensitive assay for metal ions in a sample also flows from a second advantage of the compositions of the present invention, in either its embodiment as a covalent joining of the metal ion binding protein to the photoluminescent molecule or as a non-covalent composition comprising these ingredients. The lifetimes of the fluorophores are chosen such that a significant change in anistropy will occur upon a change in lifetime of the label. Weber showed decades ago that fluorescent labels attached to proteins by short tethers often substantially reflect the overall rotational motion of the protein (see for example G. Weber, "Rotational Brownian motion and the polarization of fluorescence of solutions," Adv. In Prot. Chem. 8, 415-459 (1953)), and thus for a macromolecule with an approximately 15 nsec rotational correlation time (like apo-carbonic anhydrase), a fluorescent label with a very short or long lifetime will only display a modest change in anisotropy if its lifetime changes, according to the Perrin equation (equation (5) above). Using the Perrin equation with the change in lifetime predictable using Forster theory, we teach how to optimize the response and thus the sensitivity by choice of the label in FIG. 1. Thus fluorescent-labeled protein compositions previously disclosed in the art are unlikely to be workable compositions for use in the analytic methods of the present invention.

The use of the fluorophores disclosed in the non-covalent embodiments of the compositions of the present invention takes advantage of dissociation constants of the protein-fluorophore interaction that provide a tight binding of the fluorophore to the protein. Tighter binding of the fluorophore to the metal ion-binding protein is advantageous because a lower concentration of fluorophore may be used and thus the emission of the bound fluorophore represents a greater fraction of the total emission, and consequently one can detect a lower concentration of holo-protein, and thus of zinc or other divalent metal cation in a sample. Also use of fluorophores with higher quantum yield allows use of smaller samples overall and/or an assay that is more sensitive to smaller concentrations of analyte. Finally, use of a fluorophore with a substantial blue-shift in its emission spectrum upon binding to apo-protein provides for an advantage of broadened dynamic range for measurements of interaction of the fluorophore-protein complex with divalent metal cation analytes.

Incorporated by reference are the following two documents:

1. Elbaum, D., S. Nair, M. Patchan, R. Thompson and D. Christianson (1996) Structure-Based Design of a Sulfonamide Probe for Fluorescence Anisotropy Detection of Zinc with a Carbonic Anhydrase-Based Biosensor. J. Am. Chem. Soc. 118, 8381-8387.
2. Thompson, R. B., Z. Ge, and M. Patchan (1996) Determination of Multiple Analytes Using a Fiber Optic Biosensor Based on Fluorescence Energy Transfer. SPIE 2680, 47-56.

What is claimed is:

1. A composition comprising an apo-carbonic anhydrase protein and a photoluminescent molecule selected from the group consisting of 4-(2-hydroxyethylthio)-7-aminosulfonyl-2,1,3-benzoxadiazole and hydroxynaphthalenesulphonamide 2.

2. The composition of claim 1, wherein the apo-carbonic anhydrase protein is a human apo-carbonic anhydrase.

3. the composition of claim 1, wherein the photoluminescent molecule is 4-(2-hydroxyethylthio)-7-aminosulfonyl-2,1,3-benzoxadiazole.

4. A kit for assay of divalent metal ion concentration in a sample comprising:
(i) an apo-carbonic anhydrase protein;
(ii) a photoluminescent molecule selected from the group consisting of 4-(2-hydroxyethylthio)-7-aminosulfonyl-2,1,3-benzoxadiazole and hydroxynaphthalenesulphonamide;
said items i) and ii) being packaged in a container that prevents unwanted contamination by divalent metal ions.

5. The kit of claim 4, further comprising iii) a standard solution of a divalent metal ion that is packaged in a container that prevents unwanted contamination by divalent metal ions.

6. The kit of claim 4, further comprising iii) a buffer for maintaining the concentration of a free divalent metal ion in a solution that is packaged in a container that prevents unwanted contamination by divalent metal ions.

7. The kit of claim 6, wherein the buffer for maintaining a concentration of free divalent metal ion is nitrilotriacetic acid.

8. The kit of claim 4, further comprising iii) a chelating resin for preventing or removing unwanted divalent metal ion contamination that is packaged in a container that prevents unwanted contamination by divalent metal ions.

* * * * *